(12) United States Patent
Buljubasic

(10) Patent No.: US 12,023,051 B1
(45) Date of Patent: *Jul. 2, 2024

(54) DEVICE AND METHOD FOR PERFORMING STERNOTOMY

(71) Applicant: Neda Buljubasic, Los Angeles, CA (US)

(72) Inventor: Neda Buljubasic, Los Angeles, CA (US)

( * ) Notice: Subject to any disclaimer, the term of this patent is extended or adjusted under 35 U.S.C. 154(b) by 268 days.

This patent is subject to a terminal disclaimer.

(21) Appl. No.: 17/750,802

(22) Filed: May 23, 2022

Related U.S. Application Data

(63) Continuation of application No. 16/529,762, filed on Aug. 1, 2019, now Pat. No. 11,369,388.

(60) Provisional application No. 62/720,872, filed on Aug. 21, 2018, provisional application No. 62/713,660, filed on Aug. 2, 2018.

(51) Int. Cl.
| | | |
|---|---|---|
| A61B 17/14 | (2006.01) | |
| A61B 17/16 | (2006.01) | |
| A61B 18/14 | (2006.01) | |
| A61B 34/20 | (2016.01) | |
| A61B 18/00 | (2006.01) | |

(52) U.S. Cl.
CPC ........ A61B 17/1691 (2013.01); A61B 17/142 (2016.11); A61B 18/14 (2013.01); A61B 34/20 (2016.02); *A61B 2018/00196* (2013.01); *A61B 2018/00607* (2013.01); *A61B 2018/1412* (2013.01); *A61B 2034/2055* (2016.02)

(58) Field of Classification Search
CPC .......................... A61B 17/142; A61B 17/1691
See application file for complete search history.

(56) References Cited

U.S. PATENT DOCUMENTS

| | | | | |
|---|---|---|---|---|
| 1,763,730 | A * | 6/1930 | Lackum | A61B 17/142 |
| | | | | 30/388 |
| 5,088,472 | A * | 2/1992 | Fakhrai | A61B 17/0206 |
| | | | | 600/222 |
| 5,554,165 | A * | 9/1996 | Raitt | A61B 17/142 |
| | | | | 30/340 |
| 5,591,170 | A * | 1/1997 | Spievack | A61B 17/142 |
| | | | | 606/177 |
| 2004/0243136 | A1* | 12/2004 | Gupta | B23D 61/121 |
| | | | | 606/82 |
| 2005/0245935 | A1* | 11/2005 | Casey | A61B 17/142 |
| | | | | 606/82 |
| 2007/0123893 | A1* | 5/2007 | O' Donoghue | A61B 17/142 |
| | | | | 606/82 |

* cited by examiner

*Primary Examiner* — Christian A Sevilla
(74) *Attorney, Agent, or Firm* — Davidson Law Group, ALC; Payam Moradian

(57) ABSTRACT

Provided is a surgical saw for cutting a sternum comprising: a) a body, b) a handle attached to the body; c) a blade positioned in such way to cut the sternum when a user holds the handle, and d) a base below the blade configured to be positioned below the sternum, wherein the user places the base under the sternum and cuts the sternum with the blade.

17 Claims, 13 Drawing Sheets

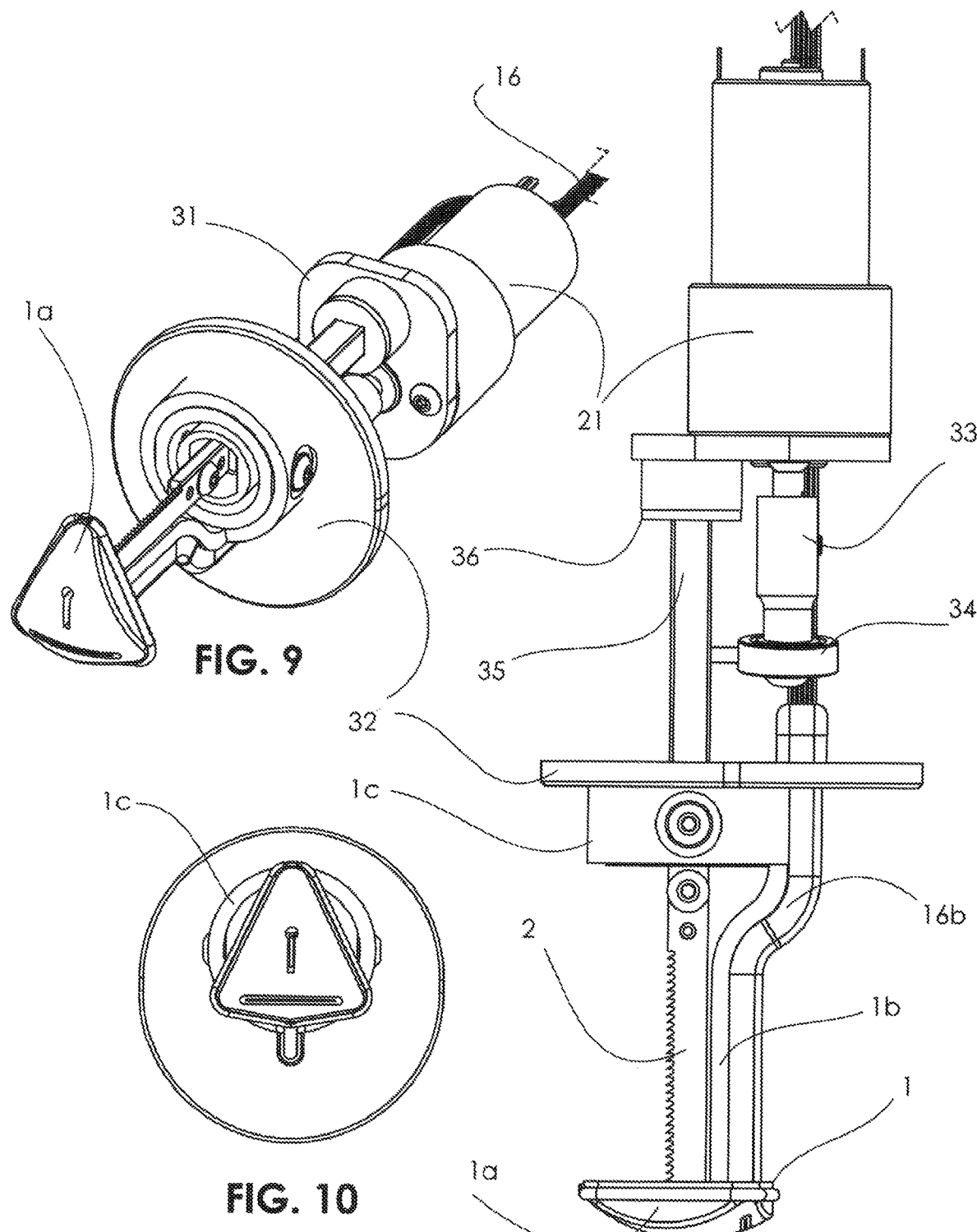

DEVICE AND METHOD FOR PERFORMING STERNOTOMY

CROSS-REFERENCE

The present application is a continuation of U.S. application Ser. No. 16/529,762, filed on Aug. 1, 2019, which claims the benefit of U.S. provisional application No. 62/713,660, filed on Aug. 2, 2018, and 62/720,872, filed on Aug. 21, 2018. All of these applications are incorporated herein by reference in their entirety.

FIELD OF THE INVENTION

This invention relates generally to surgical instrument, surgical sternal saw, more particularly, to a sternal saw that can comprise an integrated radiofrequency blade and a camera positioned in a way that would allow visualization of simultaneous separation of a sternum from underlying structures, coagulation of the periostial blood vessels and safe cutting of the sternum while visualizing tissue plane during the procedure, thereby protecting the underlying cardiac and vascular structures from mechanical injury or damage from electrocautery blade.

Background Section of the Invention

Repeated, known as re-do cardiac surgery, has dramatically higher morbidity and mortality risk when compared to first cardiac surgery or any other surgery, mainly due to the increased risk of re-do sternotomy which is at the present time performed with currently-available saws.

Currently there is no safe sternotomy saw available on the market. The saws that are currently in use are highly dependent on operator skills and require a long time (sometimes more than one hour) to cut carefully through the sternum without cutting into the heart, aorta or other vital structures, like pulmonary artery, coronary artery bypass graft conduits, assist device lines etc. Unfortunately, even in most skillful hands, proceeding with maximum patience and care, catastrophic injury to the heart, aorta and other vital structures cannot be reliably avoided. The main reason is that all of these saws require the operator to push on the saw as the saw is cutting through the bone, sternum, and then instantaneously remove the pressure and stop the saw as the back edge of the sternum is reached, trying to prevent catastrophic injury to the underlying structures. When underlying structures adhere to the back of the sternum, which is almost always the case in re-do sternotomy, the required maneuver is difficult to accomplish even by the most skillful operator. Many patients are being declined re-do cardiac surgery because of a high morbidity and mortality risk that is associated with redo sternotomy. There is a need in the art for a saw that addresses the above mentioned problems.

Summary Section Of The Invention

Provided is a device for cutting a sternum comprising: a) a body, b) a handle attached to the body; c) a blade positioned in such way to cut the sternum when a user holds the handle, and d) a base below the blade configured to be positioned below the sternum, wherein the user places the base under the sternum and cuts the sternum with the blade. The base can have a leading edge with an angle of about 20 degrees to about 60 degrees, such as 30 to 50 degrees, such as 40 degrees. A leading edge refers to the position that is towards the head of a person when the sternum is cut. The base has a leading edge that can be triangular. The device can further comprising a camera and/or light. The camera and/or light can be placed on a bottom of the base. The device can further comprise a member configured to perform cautery placed on the base in a position to contact blood vessels as the device cuts the sternum. The member can be one or more strips of a material that heats-up when electricity passes through the material. The device can further comprise a connector and/or motor housing for connecting the body to the base. The blade can be placed immediately above the base. The blade can be placed backwards relative to a perpendicular in relation to a top of the base. The blade can be placed in front of a base connector, both the blade and the base connector attached to a connector and/or motor housing that is attached to the body. The blade and the base connector can have a same angle as the connector and/or motor housing. The blade and/or the base can be visible from the top of the device when the base is in a horizontal position. The body can be non-linear and be configured to allow the user to view the base from the top. The body can have a void/opening that allows the user to view the base. The device can have two handles, with each of the handles placed on opposite sides of the body. The handles can be oriented in a perpendicular fashion to each other. The device can further comprise a vibrator that results in vibration of the blade.

Provided is a device for cutting a sternum comprising: a) a body, b) a first and a second handle attached to opposite sides of the body; c) a blade positioned in such way to cut the sternum when a user holds the handles, and d) a base below the blade configured to be positioned below the sternum, wherein the user places the base under the sternum and cuts the sternum with the blade and the base is visible from a top of the device when a leading edge of the base is positioned below the sternum.

Provided is a device for cutting a sternum comprising: a) a body; b) a handle attached to the body; c) a blade positioned in such way to cut the sternum when a user holds the handle; d) a base below the blade configured to be positioned below the sternum; and e) an electronic connection to the base to carry power and/or video signal to and from the base; wherein the user places the base under the sternum and cuts the sternum with the blade. The electronic connection can be a wire that is placed behind the blade. A cautery member can be placed on the base comprising one or more strips of a material that heats-up when electricity or radiofrequency passes through the material. The base portion below the member can extend out further than the cautery member to insulate tissue that is below the base. The device can further comprise a connector for connecting the body to the base, with the blade placed in front of the connector in a direction of cutting the sternum. The blade is placed at a backwards angle (top of the blade further back) relative to a perpendicular in relation to a top of the base. The blade and/or the base can be visible from a top of the device when the base is in a horizontal position. The device can further comprise at least one switch on each handle, with one switch on the first handle configured to power the blade and one switch on the second handle configured to power operating of a heating element of the base for performing cautery. The device can comprise a post portion of a body extending upward from the blade, the body further comprising a segment with a void where the blade is visible during operation through the void attached to the post, and two handles, with one handle attached to the segment with the void and another handle to the post and/or the void. The device can comprise the base attached to the body with a connector, with the body and/or handle extending on two different sides of the blade. The device can have two handles that are not directly attached to each other.

Provided is a device for cutting a sternum comprising: a) a body, b) a first and a second handle attached to opposite sides of the body; c) a blade positioned in such way to cut the sternum when a user holds the handles, and d) a base below the blade configured to be positioned below the sternum, wherein the user places the base under the sternum and cuts the sternum with the blade and the base is visible from a top of the device when a leading edge of the base is positioned below the sternum.

Provided is a device for a device for cutting a sternum comprising: a) a body, b) a blade positioned in such way to cut the sternum when a user holds the device, and c) a triangular base below the blade configured to be positioned below the sternum, wherein the user places the base under the sternum and cuts the sternum with the blade and the base is visible from a top of the device when a leading edge of the base is positioned below the sternum.

Provided is a surgical saw comprising of a body having a saw blade vertically oriented, an electrocautery blade, two handles with two switches independently controlling the saw power and optionally an electrocautery blade. A built in camera positioned behind the electrocautery blade aids in visualizing the dissecting plane under the posterior sternal plate.

Provided is a saw for performing sternotomy. This device can be a sternal saw and optionally further can be configured to perform electrocautery (a heat generated by a high-voltage, high-frequency alternating current). The device, while safely cauterizing, can achieve successful hemostasis, and separate the back plate of the sternum from the adjacent underlying soft tissues, primarily cardiac structures, preventing cardiac injury and bleeding.

A user, typically a heart surgeon, can perform three or more simultaneous and critical tasks with the device during surgery: 1) safely cut through the sternum under direct visualization of the cutting plane; 2) separate the bony structures of the sternum from underlying soft tissues, including the heart and blood vessels such as the aorta and pulmonary artery; 3) prevent bleeding by using the optional built-in cauterizing device allowing the surgeon to operate in a blood-free field and reduce blood loss; 4) perform sternotomy under direct visualization with the use of an optional built-in camera; 5) perform both primary and redo sternotomy faster when compared to the presently-available sternotomy saws.

The built-in oscillating saw cuts the sternum, which is already separated from underlying cardiac structures, through a combination of cutting of the tissue by the electrocautery tip edge and lifting of the sternum by the operator. With the motion of lifting of the sternum away from the underlying structures by an operator, the tapered and forwardly-positioned, "arrow like" cautery device slides under the sternum while cutting and separating the posterior plane of the sternum from the heart and other structures. This allows the built-in sternal saw, which is positioned behind and above the cautery device, to cut the sternum now separated from underlying structures without any risk of sustaining injury to the heart, great vessels or any other thoracic structure. The thin leading edge of the cautery tip allows safe separation of the substernal structures from the sternum while the thick trailing tapered edge separates the vital structures from the saw, eliminating any chance that the saw can cut the vital structures, which can lead to serious and sometimes fatal injury and uncontrolled bleeding. By cauterizing the periostal blood vessels, the saw reduces bleeding, blood loss, improves visualization and makes the rest of surgical dissection easier, faster, safer and less dependent on the operator's skills.

The sternal saw can be powered by electricity or compressed air. The saw can have a radiofrequency blade oriented perpendicular to the saw blade. The structures under the sternum including heart, blood vessels and other mediastinal structures can be protected from the saw blade by a blunt, arrow-like, kite-like, triangular, or similar shaped dissecting "base," which on its superior aspect of the leading edge can have a cautery blade. The dissecting "base" containing the radiofrequency blade in its tip, can be covered inferiorly by an electrical insulator that prevents the underlying tissue/organ structures from being damaged by the radiofrequency blade. The electrical insulation can prevent micro- or macro shock to the heart that could cause injury to the heart or irregular heart rhythm that may make the patient unstable. The thermal insulation can prevent thermal injury to the heart, aorta or other vital mediastinal structures. The tip of the base can be made of a transparent material that allows the built-in video camera to produce images of the tissue plane (similar to the cameras for saphenous vein harvest or endoscopy).

The device can be a handheld device. In one embodiment, the device can have two handles. The first of the handles is in the back of the saw and would be grasped by the operator using her dominant hand and has a switch(s) that can be used to control the saw movement (activation of the saw and cutting of the sternum). Both, the saw and the electrocautery can be activated by any suitable control switch (one or more switches). The speed of the saw can be controlled by varying the pressure applied to the switch by the operator's finger (usually index finger of the dominant hand). Increasing the pressure applied to the switch results in increasing the speed (power) of the saw. In another embodiment, in addition to the saw switch, the saw can have a safety switch that has to be turned off (inactivated) to activate the saw and start cutting the sternum. The safety switch can be positioned on one or both sides of the saw handle in such a way that both left- and right-handed operators can use the saw safely by eliminating the possibility of either a patient, an operator or an assistant being injured due to an accidental activation of the saw. In another embodiment, the safety switch can be positioned on the top of the handle opposite to the saw switch. In another embodiment, a single safety switch can be used to prevent accidental activation of the saw, electrocautery or the light source.

In another embodiment, the saw has a second handle at the front of the saw that is grasped by the non-dominant hand and used to lift the sternum away from the heart and other adjacent structures. In a further embodiment, the saw has a switch at both sides of the handle that is used to control the electrocautery blade by both right- and left-handed operators.

In another embodiment the electrocautery blade can be connected to a switch that is activated when an electrocautery switch is engaged and/or backward pressure (resistance) is sensed as the saw is advanced against the soft tissues under the sternum. This switch can regulate or interrupt the current delivered to the electrocautery blade and it can prevent excessive and unnecessary heat generated when the electrocautery is not resisted by the soft tissue. In another embodiment, the switch is not connected to the electrocautery blade itself but is connected to the beam (connector and/or motor housing) that is connecting the base of the saw and the body of the saw.

In another embodiment, the sternal saw has a disposable saw blade that is oriented forward and upward and is used to cut the sternum after it is separated from the structures underlying the sternum. In another embodiment, the disposable or reusable saw blade is visible from the top of the saw and the line of vision of the operator to the blade is unobstructed unlike most current saws on the market. An unobstructed view of the blade and the cutting plane allows much more precise maneuvering of the saw to facilitate a mid-sternal cut.

In another embodiment, the dissecting baseplate containing the electrocautery blade can be connected to the body of the saw by a post made of hardened steel, titanium or another material that has extremely high tensile strength to be able to sustain the force applied and to prevent bending during lifting and cutting of the sternum during the use of the saw. To ensure easy sliding along the cut made in the sternum, the width of the connecting post has to be smaller than the width of the cut made by the saw blade. In addition to the width of the post, the front of the post can be tapered and rounded to reduce resistance and facilitate sliding along the sternotomy cut.

In another embodiment the electricity powered saw is powered by a rechargeable battery that can be sterilized and attached and detached from the handle or the body of the saw by a button controlled latching mechanisms. In yet another embodiment the electrical saw is powered by an outside power source that is connected to the saw by a flexible insulated electrical cable that can be disposable or reusable after sterilization.

In another embodiment compressed air can be used to power the saw. In order to power the saw with the compressed air the saw has to be connected to pressurized air outlet. A flexible high pressure hose that is easily sterilized can be used to provide the compressed air. Both ends of the hose can be quickly connected and disconnected with the use of the quick connect connectors.

The saw that integrates the cutting saw blade, electrocautery blade and endoscopic camera may use appropriate console(s). One, two or three separate consoles can be connected to the saw and used to power the saw, to power the electrocautery blade and produce an image that can be displayed on the console screen or on the operating room audiovisual system screen(s). The electro surgical unit will be used to enable and control the electrocautery blade power and voltage. In addition to a cable connected to the saw power unit and the electrocautery unit, there has to be a separate grounding pad connecting the patient and the electrosurgical unit for a complete electrical circuit. In one embodiment, the saw will also be connected to an electrical power source supplying electrical power to the saw blade, or compressed air power source to power the saw for this purpose. In another embodiment, the saw can be powered by a rechargeable battery that can be sterilized and attached and detached from the saw by the use of a latching mechanism that has two or more electrical contacts. The third connection can be to an endoscopic video camera that is built into the base of the saw. A high definition video camera can connect to an image processing unit that itself connects to the video display screen. The image processing unit can have high definition (HD) display or HD output to the operating room video system.

In another embodiment, the entire dissecting baseplate could be detached from the saw and be replaced with a disposable one for use with each patient. In a further embodiment, only part of the dissecting baseplate would be disposable and the majority of the baseplate including the light source and camera would be reused. The front part of the dissecting baseplate would be disposable. In particular, the electrocautery plate may be disposale and/or the transparent plastic cover can be detached from the saw baseplate in order to be replaced by disposable parts. In another embodiment, the device can be used without the saw function to separate the back plate of the sternum from the underlying soft tissue plate

BRIEF DESCRIPTION OF THE DRAWINGS

FIG. 8 illustrates a perspective view of reciprocating engine.
FIG. 9 illustrates a perspective view of reciprocating engine.
FIG. 10 illustrates a bottom view of reciprocating engine.

DETAILED DESCRIPTION OF THE INVENTION

Figure 1:
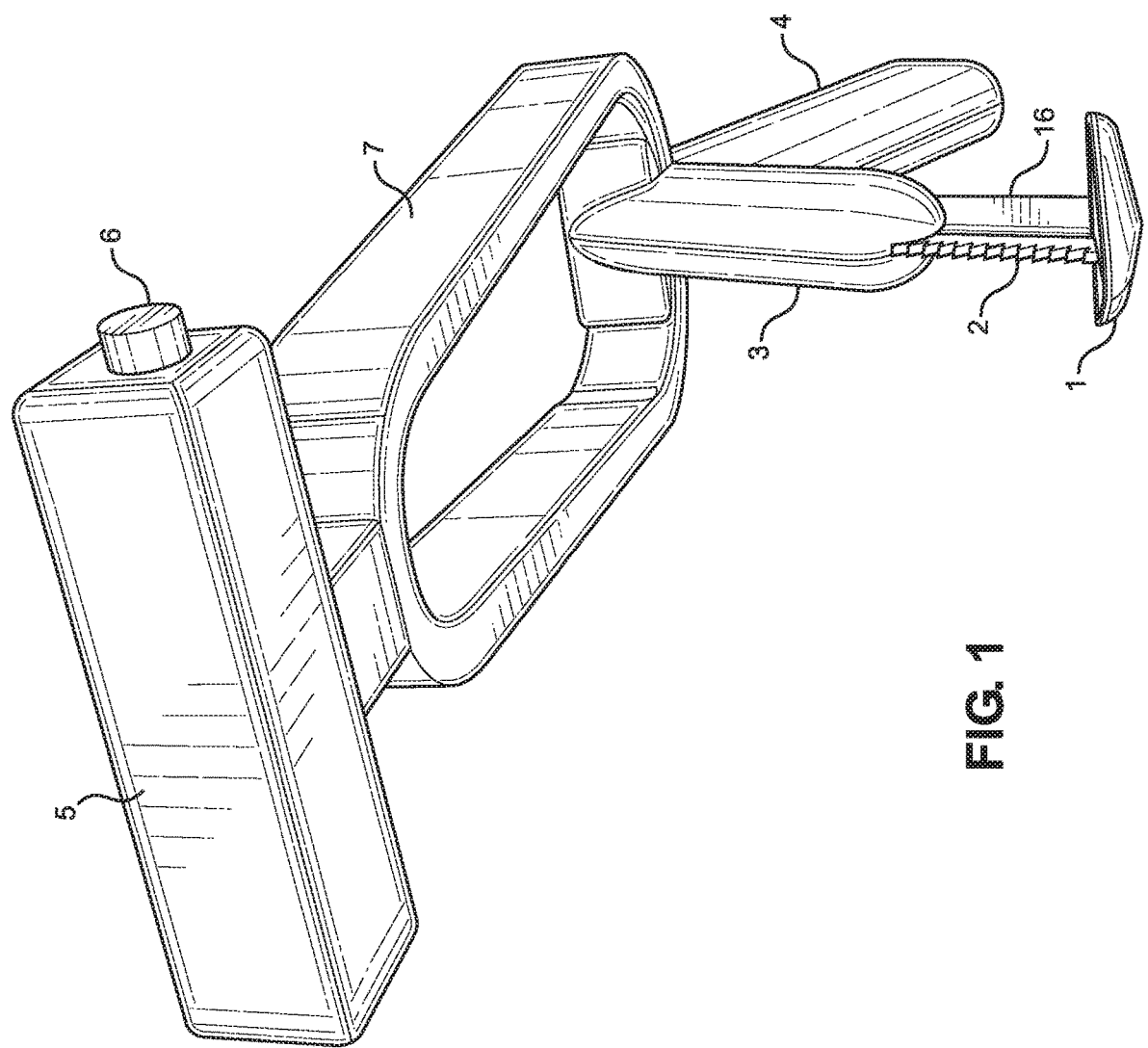
FIG. 1 illustrates a bottom perspective view of the device.

FIG. 1 illustrates a bottom perspective view of the device. The saw is shown with base 1, a blade 2 positioned on top of base 1, a post and/or motor housing 3 for connecting to both base connector 16 and blade 2. Body 7 is positioned on top of post and/or motor housing 3. The body 7 is connected at one end to handle 4 and at another end to handle 5.

The base 1 is configured to be placed below the sternum as the device cuts the sternum. The base 1 is configured to separate the sternum from the tissue below. The base 1 can have a leading angular edge (such as triangular/V-shaped) that is oriented towards the person's head as the saw cuts the sternum. The angle can be about 10 degrees to about 50 degrees, such as about 20 to 40 degrees. The top of the base 1 can be flat and bottom of the base 1 can be curved. The base 1 can have straight sides with curved edges. The base 1 can be a triangular shape with a maximum height of 2 mm to 10 mm. The maximum front to back length of the base 1 can be 10 mm to 40 mm. The maximum side to side width of base 1 can be 10 mm to 40 mm. The base 1 generally can have a maximum width to maximum height ratio of 2 to 5.

Placed above the base 1 is blade 2, which is configured to cut the sternum. Blade 2 can be serrated. Blade 2 can be placed with a backward orientation (in relation to top of base 1) with an angle of 5 degrees to 40 degrees, such as 10 to 30 degrees relative to the perpendicular. Base connector 16 is positioned behind blade 2. The base connector 16 and the base 1 can be made from one piece of material or can be two separate pieces. Wires for carrying power and signals can go though the base connector 16 to base 1 or through another connection. An optional vibrator 17 can be placed in connector and/or motor housing 3. Post and/or motor housing 3 can have a slot on the bottom for attachment of blade 2. Blade 2 can have an opening on top that makes blade 2 attach to a locking mechanism present in the slot of post 3. Similarly, a slot can be present on top of base 1. The blade 2 can exhibit reciprocating motion or oscillating motion. The blade can also operate with vibrational motion alone, or in combination with any of the above modes of blade movement. In one embodiment, the device has only a vibration generating motor 17. In another embodiment, in addition or instead of the vibrator, the device can have another motor that generates non-vibrational motion, such as a reciprocating or oscillating motion.

As illustrated, base connector 16 is attached to bottom of post and/or motor housing 3. Top of connector and/or motor housing 3 is attached to the body 7. The body 7 can have a void so that base 1 is visible to a surgeon during surgery. As illustrated in FIG. 1, body 7 is oval-shaped to allow for a void in the middle so that base 1 is visible during surgery. Body 7 can also be linear, such as by having a single curved piece (rather than a closed shape). To provide for further visibility, base 1 can also be made from a transparent or translucent material.

The proximal end of the body 1 where the top of post and/or motor housing 3 is attached, can also be attached to a handle 4. The handle 4 as illustrated is oriented downwards in relation to the body, such as at about 5 to about 40 degrees, such as 10 to 30 degrees. The handle 4 can be perpendicular to post and/or motor housing 3. The distal portion of the body 1 can be attached to handle 5. The handle 5 can be oriented in a perpendicular fashion to handle 4. The handle 5 can be in shape of a T. Button 6 on the handle 5 is visible in this view and can be used to control one or more functions of the device. Button 6 can, for example, function as a safety button or turn on the cautery member 15.

Figure 2:
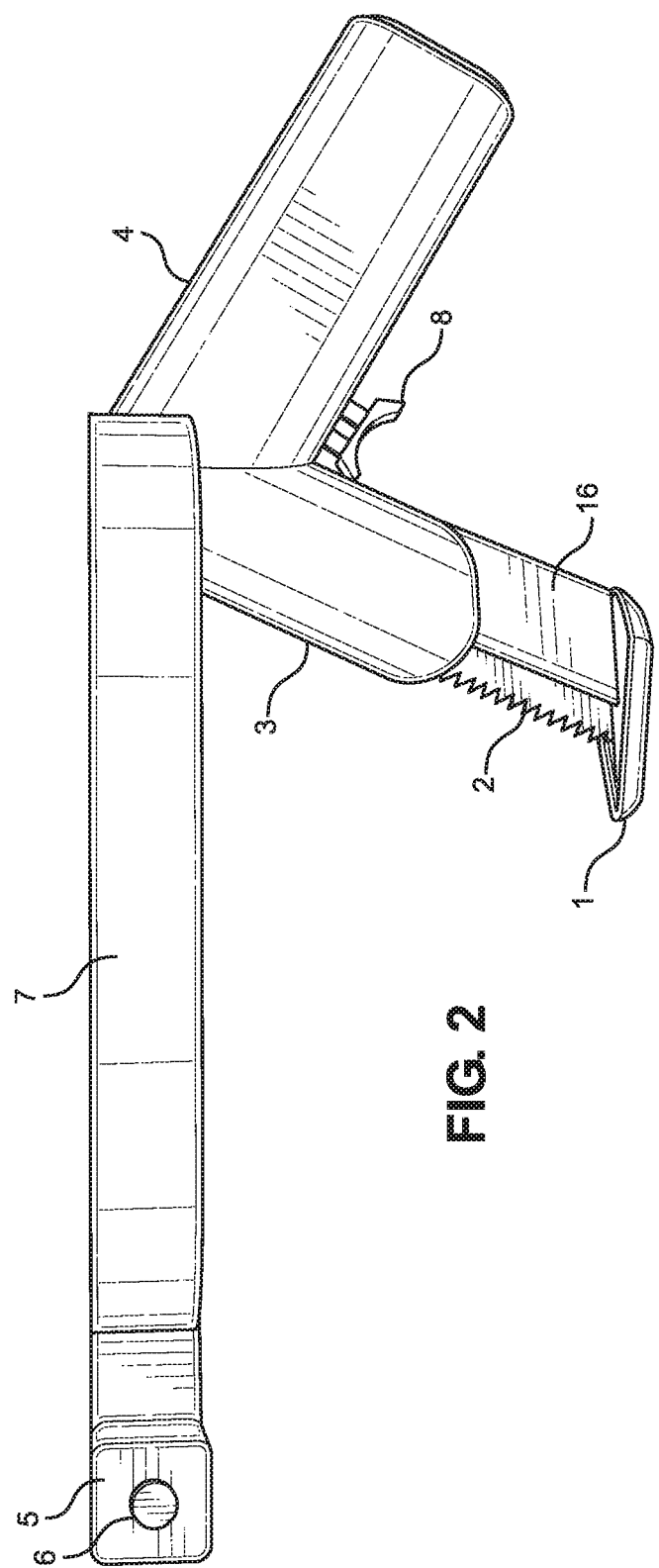
FIG. 2 illustrates a side view of the device.

FIG. 2 illustrates a side view of the device. This view illustrates the angles of the different components relative to each other. In relation to the body 7 being horizontal, the handle 4 can come point downward 5 to about 40 degrees, such as 10 to 30 degrees. The handle 4 can be approximately perpendicular with post and/or motor housing 3, which can also extend 5 to about 40 degrees, such as 10 to 30 degrees in front of a perpendicular line from the body 7. The handle 4 can have a trigger 8 on it that can be controlled by a finger. The trigger 8 can allow a user to vary the speed of the saw, typically the back and forth speed of blade 2. Button 6 illustrated on handle 5 can act as a safety button that activates the trigger 8 when pressed. Alternatively, Button 6 can activate cautery member 15.

Figure 3:
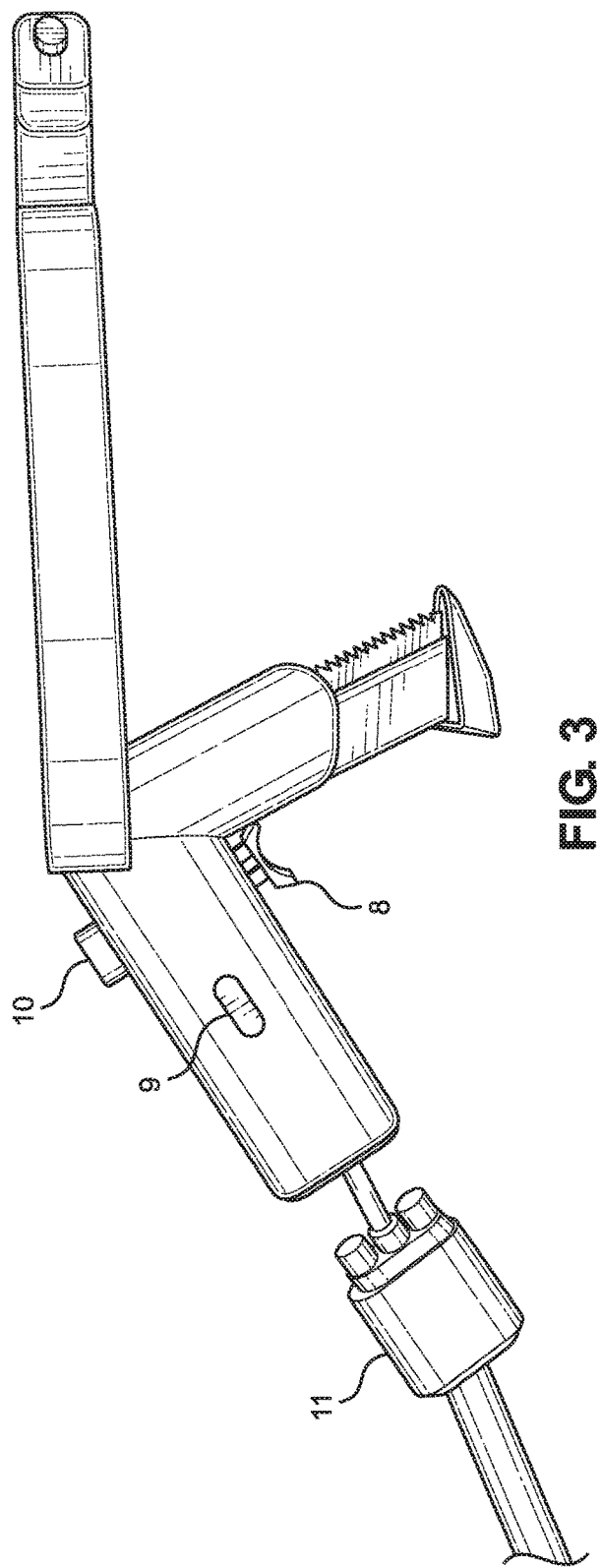
FIG. 3 illustrates a side view of the device.

FIG. 3 illustrates a side view of the device. Illustrated in this view are additional buttons such as button 9 and 10, which can be configured to control for example the camera, lighting, and power to the device. An external power source 11 can be attached to end of the handle 4. The power source 11 can carry electric power or pressurized air (pneumatic). Optionally, a rechargeable battery 26 can be placed inside handle 4 or be externally attached to the handle 4. Cables for carrying power, video signals and/or other non-power related signals can have an interface at end of handle 4. The end of the handle 4 can have a port for attaching the power source and additional cables/wires.

Figure 4:
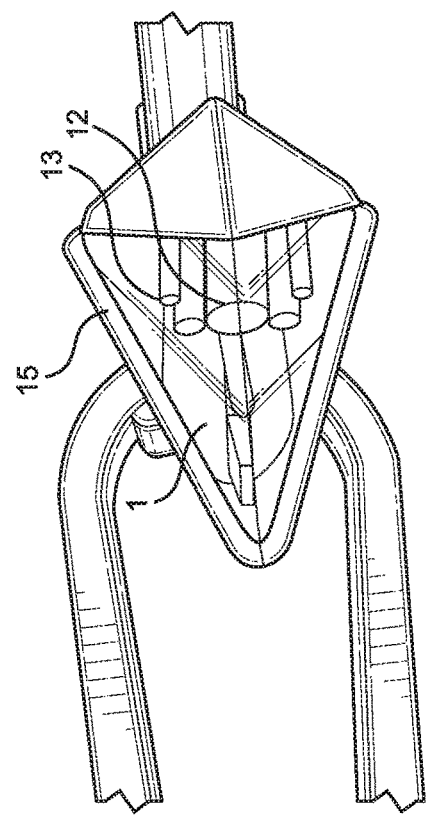
FIG. 4 illustrates a bottom view of the device.
Figure 5:
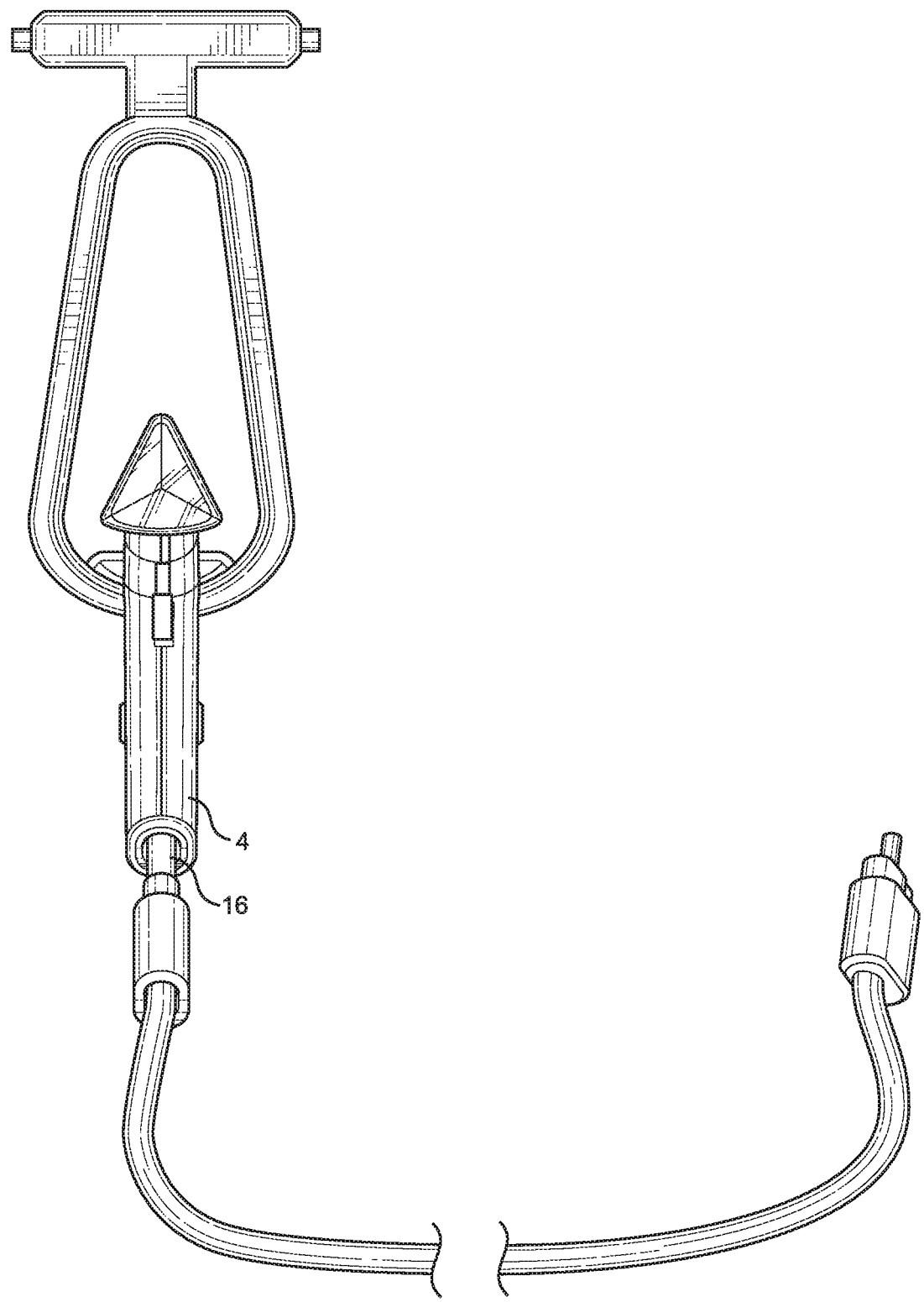
FIG. 5 illustrates a port at end of a handle for interfacing with an outside cable.
Figure 25:
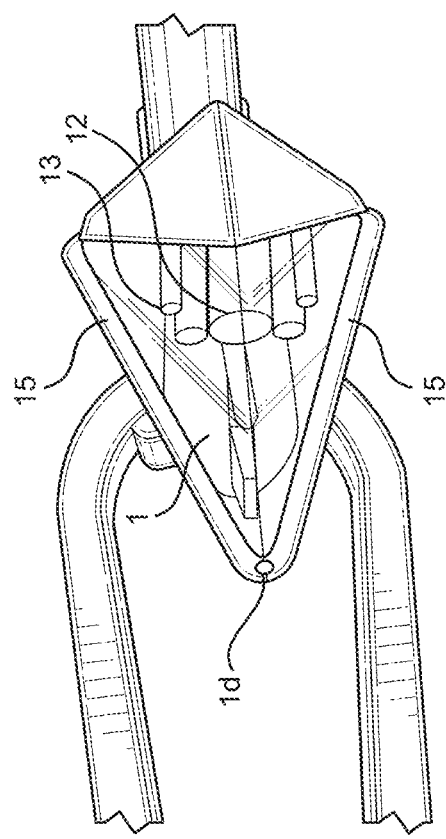
FIG. 25 illustrates a transparent window on the leading edge of the base.

FIG. 4 illustrates a bottom view of the device. Illustrated in this view is the bottom of the base 1. Base 1 can have a cautery member 15 that is configured to burn blood vessels. The cautery member 15 can be in form of material, such as metal or a carbon material, that heats up when current or radiofrequency pass through to power the heating element, the heating reaching a sufficient temperature to burn blood vessels. Strips of metal or other material such as carbon based material that is configured to act as cautery can be placed on the leading edge of base 1. FIG. 4 also illustrates light source 13 and camera 12. The camera 12 can send video back that can be displayed on a screen. Wires carrying video and power can pass through base connector 16, connector and/or motor housing 3, and handle 4, and be connected to an outside source through a port 16 at end of the handle 4. As illustrated in FIG. 4, camera 12 can be placed behind a transparent portion of the base 1, which acts as a shield for the camera 12. FIG. 5 illustrates a port 16 at end of handle 4 for interfacing with an outside cable. FIG. 25 illustrates a transparent circular opening 1*d* placed on the leading edge of base 1 as a cut-off portion of the cautery member 15.

Figure 6:
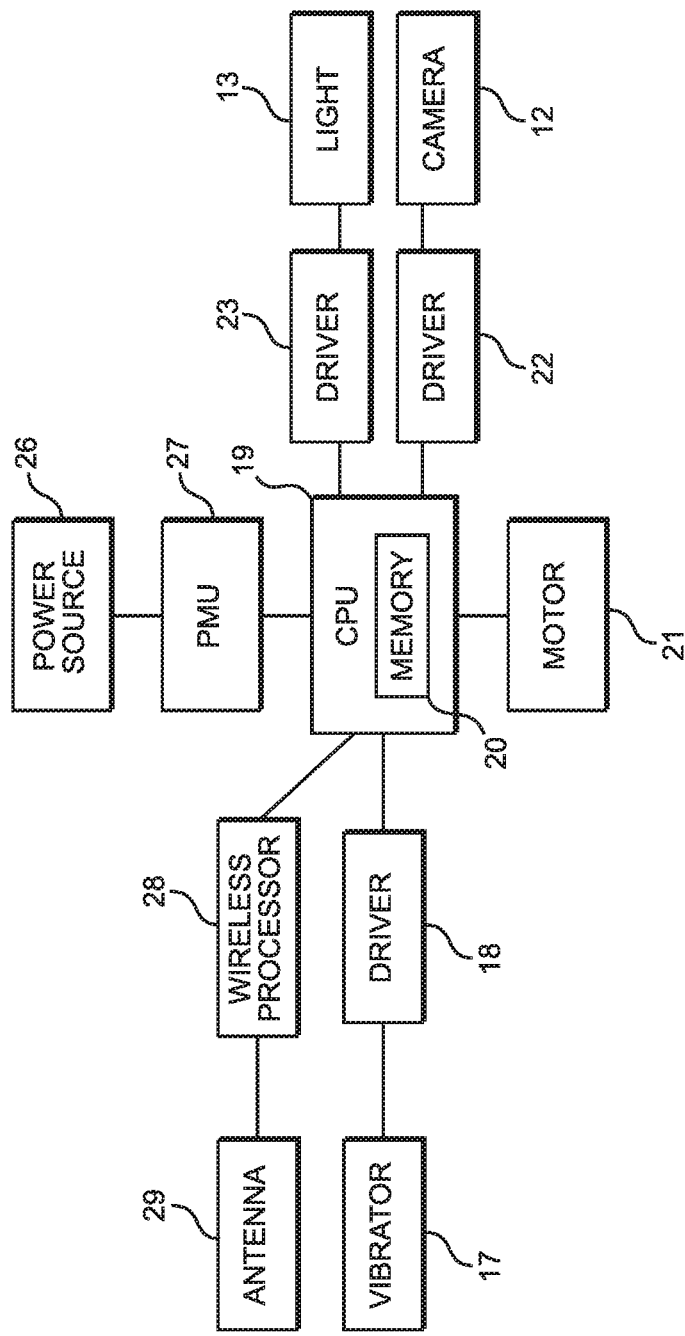
FIG. 6 illustrates various exemplary electronic components of the device.

FIG. 6 illustrates various electronics components of the device. The device can have a power source 26, typically in form of a rechargeable battery. Alternatively, an external source of power can be used. The device can also supply radiofrequency as the source of power. The device can further have a processor 19 for fetching and executing instructions present on a memory 20. The device can have a camera and a light source (such as light emitting diode), which can be regulated by drivers 22 and 23. The device can further have a power management unit 27 for regulating flow of power/current to the various components. The device can have a wireless processor 28 configured for communication with a wireless protocol, and an antenna 29. The device can also have an optional vibrator 17 that can be controlled with a driver 18. The device can also have an additional motor for generating a non-vibrational motion.

Figure 7:
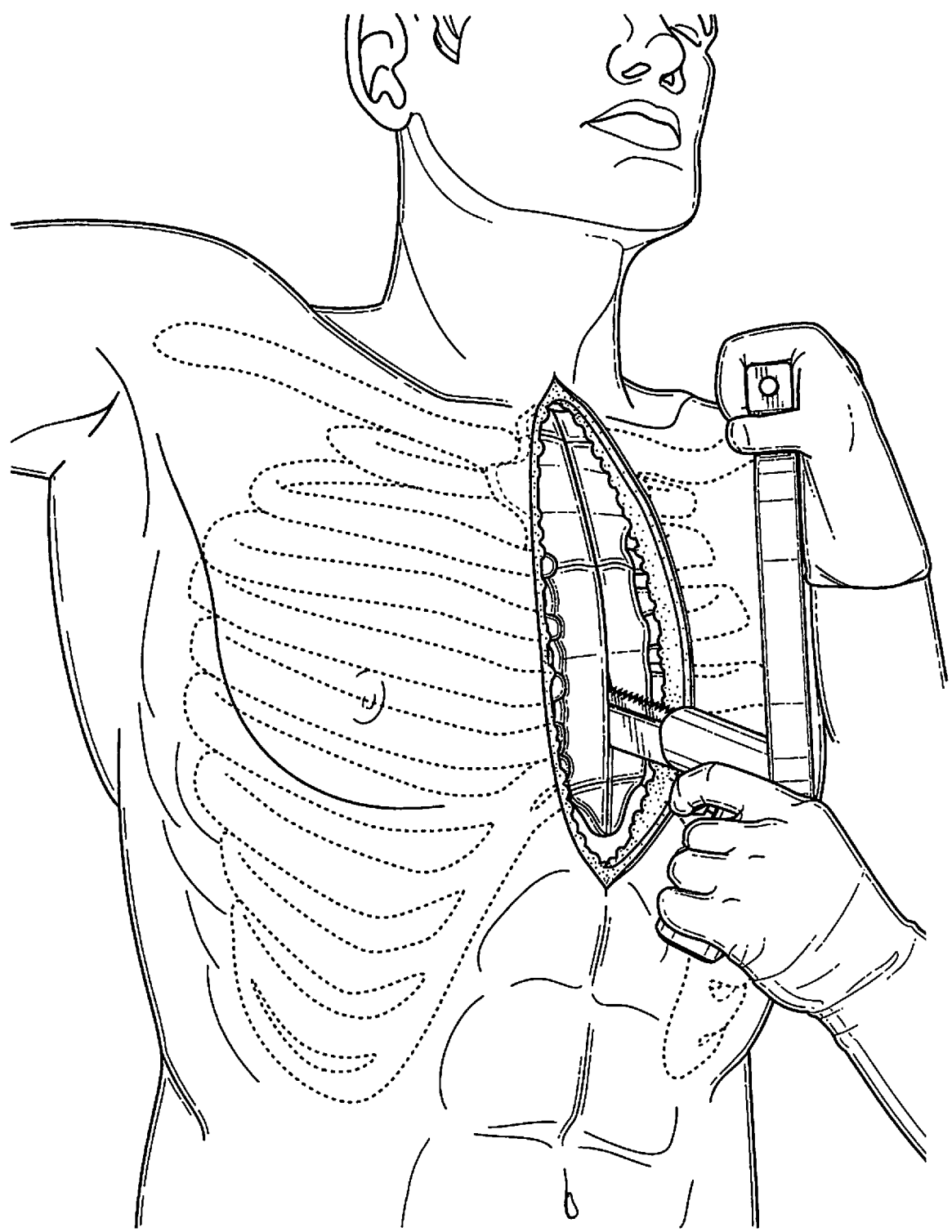
FIG. 7 illustrates the saw cutting the sternum.
Figure 24:
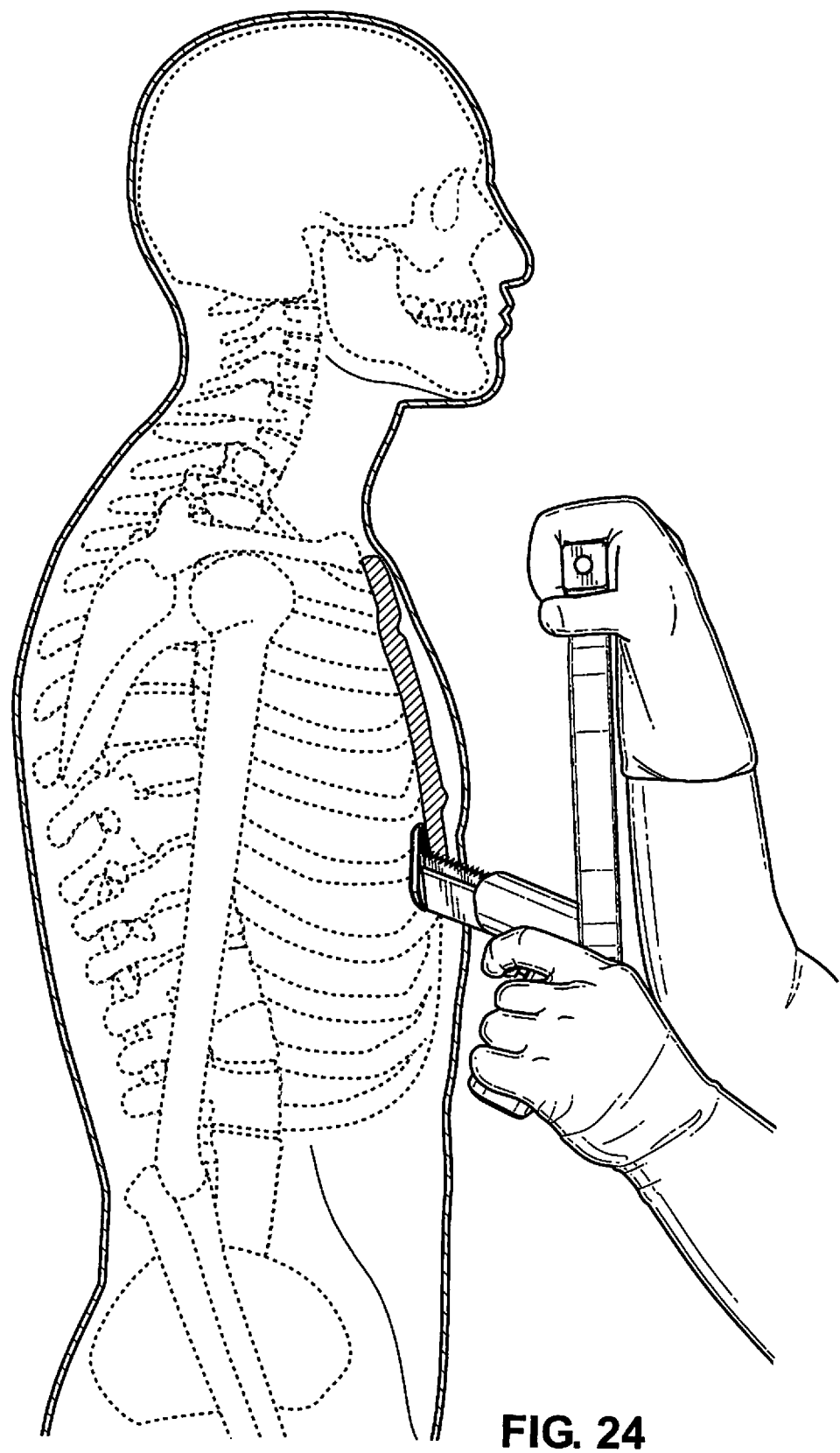
FIG. 24 illustrates the saw cutting the sternum.

A surgeon uses the device by placing the base 1 under the sternum, as illustrated in FIGS. 7 and 24. The front of the base 1 extends to front of the blade 2. The surgeon can optionally pull the sternum upwards using the front of base 1. After placement of base 1 in the proper position, the saw can be activated by pressing the trigger 8. A safety switch and/or a power switch may also be activated before pulling the trigger. Depending on the design of the saw, the blade 2 can exhibit the desired motion/movement when the trigger is pressed. If the surgeon desires, the surgeon can also activate optional lighting 13, cautery, 15 and/or camera 12 placed on the base. The base 1 can have a leading triangular (V-shaped) edge. The triangular (V-shaped) edge can be round or pointed. One or more strips of a material, such as a conductive metal or carbon, can be placed on the leading edge. When activated, the strips heat up to a sufficient temperature to perform cautery of blood vessels as the saw cuts the sternum. The surgeon can also turn on optional lights 15 and/or the camera 12 located on the bottom of the base 1. The camera can send signals back with a cable or with a wireless protocol, such as WiFi. The surgeon keeps on moving the saw towards the head of the person by using handles 4 and 5 to guide the saw. Use of two handles also allows for better control and for lifting the saw. In addition, one handle 4 can have a button/switch/trigger 8 for controlling the blade 2 and another handle 5 can have a button/switch 6 for controlling the cautery member 15.

FIGS. 8 to 10 illustrate mechanical components of a saw that operates with a reciprocating motion. To generate a reciprocating motion, a crank, a Scotch yoke type drive, a swash plate type drive, a captive cam or eccentric, barrel cam, or other rotary to linear drive may be used. FIG. 8 illustrates a side view of the saw blade. Illustrated in this view are base 1, saw support 1b, blade 2, base connector protective shield 16b, DC (Direct Current) gear motor 21, blade support mounting plate 32, shaft 33, shaft ball bearing(s) 34, linear shaft 35, square linear bearing 36, and disposable base cover 100. The movement of motor 21 results in rotation of shaft 33, which results in movement of ball bearings 34. The head of shaft 33 can have a variable shape that can create a three dimensional motion. The connecting shaft between ball bearings 34 and linear shaft 35 results in a linear back and forth motion. Shaft 35 moves back/forth in a linear fashion, resulting in an up/down motion of the blade 2. FIG. 9 illustrates a perspective view of reciprocating engine. Illustrated in this view are base connector 16, DC gear motor 21, motor chassis 31, blade guard mounting plate 32, and disposable base cover 100. FIG. 10 illustrates a bottom view of reciprocating engine. Illustrated in this view is base support mounting 1e.

Base 1 can be made of an insulating material. Examples of insulating materials include plastics, ceramics, or carbon fiber. The cautery member 15, as illustrated in FIG. 8, can be placed on the sides and/or leading edge of base 1. Base 1 can have a portion that extends out under cautery member 15, minimizing contact of cautery 15 with tissue that is below the base.

Figures 11, 12, 13:
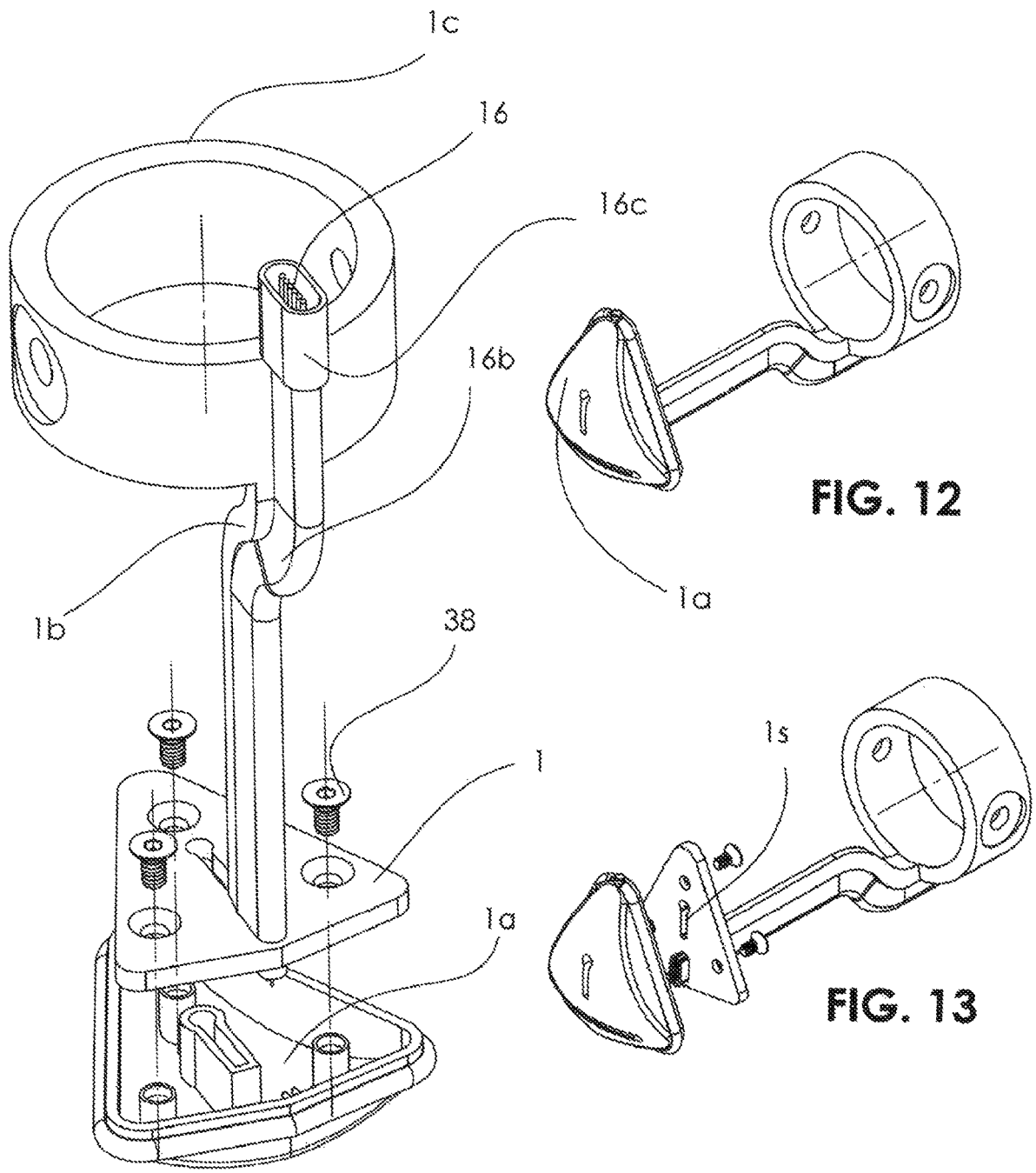
FIG. 11 illustrates a side perspective exploded view of blade support.
FIG. 12 illustrates a view of blade support.
FIG. 13 illustrates a top perspective exploded view of blade support.

FIG. 11 illustrates a side perspective exploded view of blade support. Illustrated in this view are base 1, saw support 1b, base support mounting 1c, base connector 16, base connector protective shield 16b, base connector receptacle 16c, base cover mounting screw 38, and base cover 100. Base support mounting 1c can be used to detachably or irreversibly attaching the assembly with holding blade to the rest of the saw. Detachable attachment allows for only discarding the blade assembly after use and/or changing the type of blade that is needed. Base connector 16 can form an electronic connection a wire on the saw so that electricity is delivered to base 1 and/or video is received from base 1. FIG. 12 illustrates a view of blade support. Illustrated in this view are nib 2e and nib guide 2f. FIG. 13 illustrates a top perspective exploded view of blade support. Illustrated is a blade tip clearance slot 1s. The entire assembly of FIG. 11 can be disposable. The assembly can be secured to the saw through the openings on the base support mounting 1e.

Figures 14, 16:
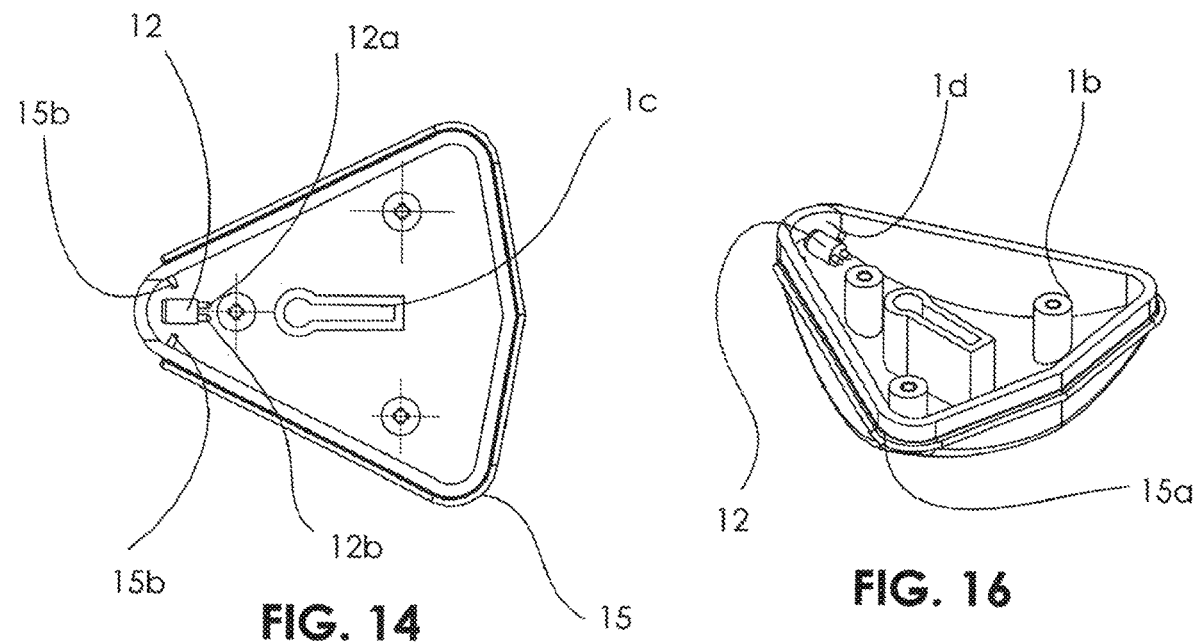
FIG. 14 illustrates a top view of disposable base cover.
FIG. 16 illustrates an isometric top view of disposable base cover.
Figures 15, 17:
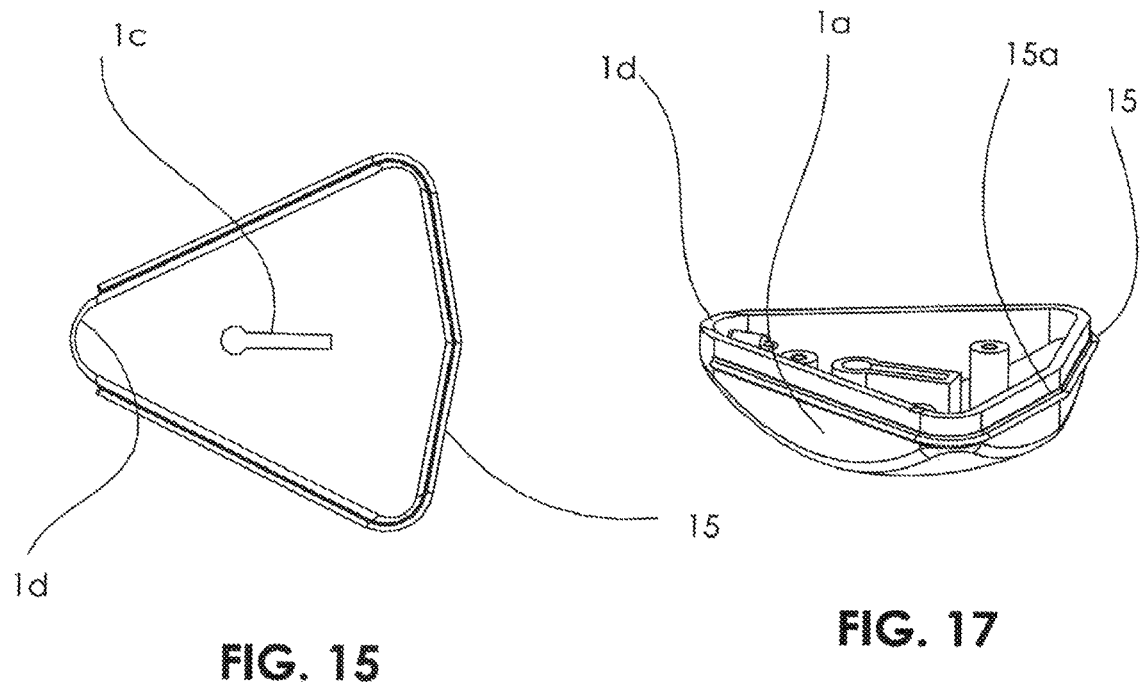
FIG. 15 illustrates a bottom view of the base cover.
FIG. 17 illustrates an isometric side view of base cover.

FIG. 14 illustrates a top view of the base cover. Illustrated in this view are camera 12, camera video and power cable 12a, camera video light and power cable 12b, cautery member 15, Cautery member ceramic insulator 15a, cautery member connector 15b, clear camera window 1d, blade tip clearance slot 1s, and disposable base mounting 1b. As illustrated in this drawing, camera 12a is placed behind a transparent window 1d while facing front of the saw. Cautery member 15 can be positioned on the sides of base 1, extend behind base 1, and/or be on the leading edge. As illustrated, Cautery member 15 is a single piece of strip that goes around the sides and back of base 1, and is attached with connector 15b. The base 1 can have a cavity on the inside that allows for placement of the wiring and camera 12a. FIG. 15 illustrates a bottom view of the base cover. Illustrated in this drawing are cautery member 15, cautery member ceramic insulator 15a, and blade tip clearance slot 100b. The insulator 15a is placed on the bottom of cautery 15, and protrudes out further to the side to avoid contact between cautery member 15 and tissue that is below base 1. FIG. 16 illustrates an isometric top view of disposable base cover, which can be changed after use. Illustrated in this view are cautery member connector 15b, disposable base cover 100, and disposable base mounting 100a. FIG. 17 illustrates an isometric side view of base cover, showing cautery member 15, cautery member ceramic insulator 15a, and cautery member connector 15b. FIG. 25 illustrates a leading edge of base 1 where cautery member 15 covers the leading edge other than a circular window 1d that is in front of the camera.

Figure 18:
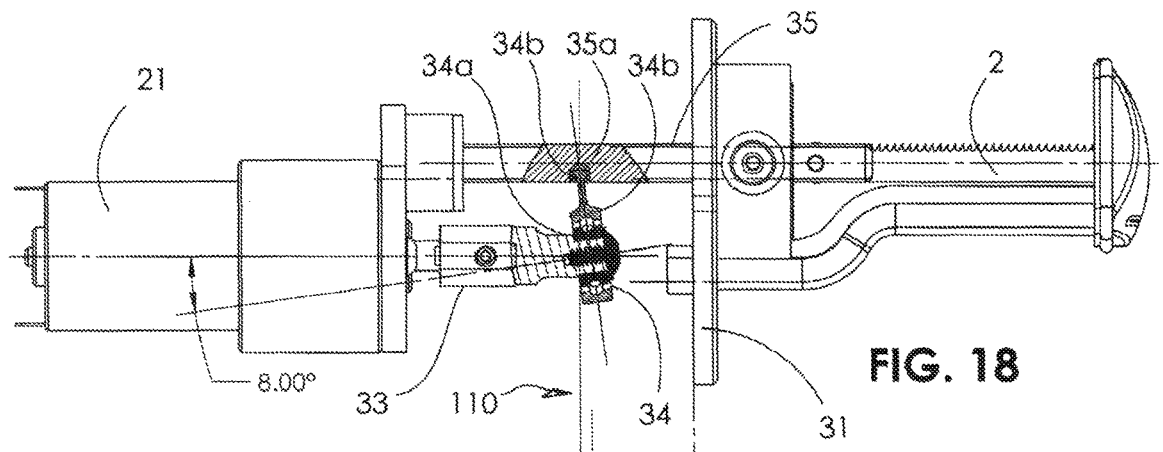
FIG. 18 illustrates a far side view of reciprocating saw.

FIG. 18 illustrates a side view of a reciprocating saw, partially sectioned (shaft, item 33 at 0 or 360 degree rotation position). Illustrated in this drawing are blade 2, motor 21, motor chassis 31, shaft 33, ball bearing 34, ball bearing inner ring (fixed to shaft 33) 34a, ball bearing outer ring 34b pivoting plunger with joint ball 35b, linear shaft 35, linear shaft receptacle joint cup 35a, and linear shaft 35. The angle of the plunger can vary from the horizontal, such as a maximum of plus/minus eight degrees between the horizontal and a line along the plunger 35b.

Figure 19:
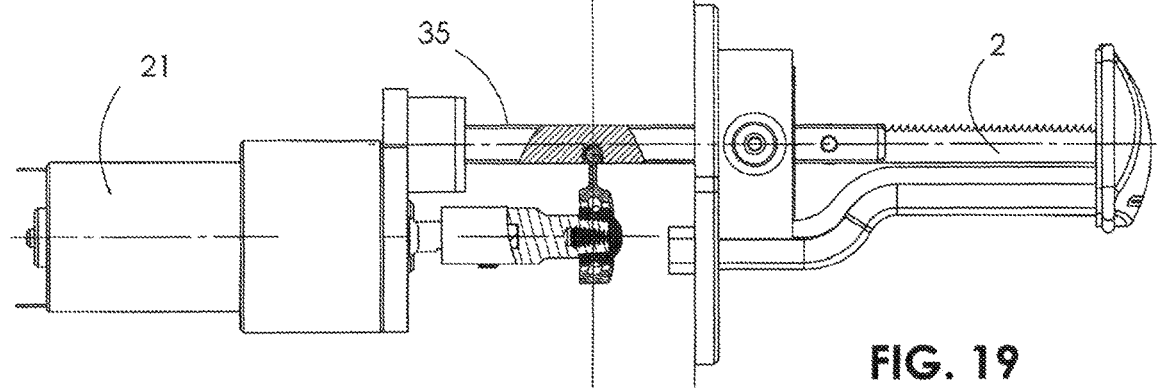
FIG. 19 illustrates a side view of reciprocating saw.
Figure 20:
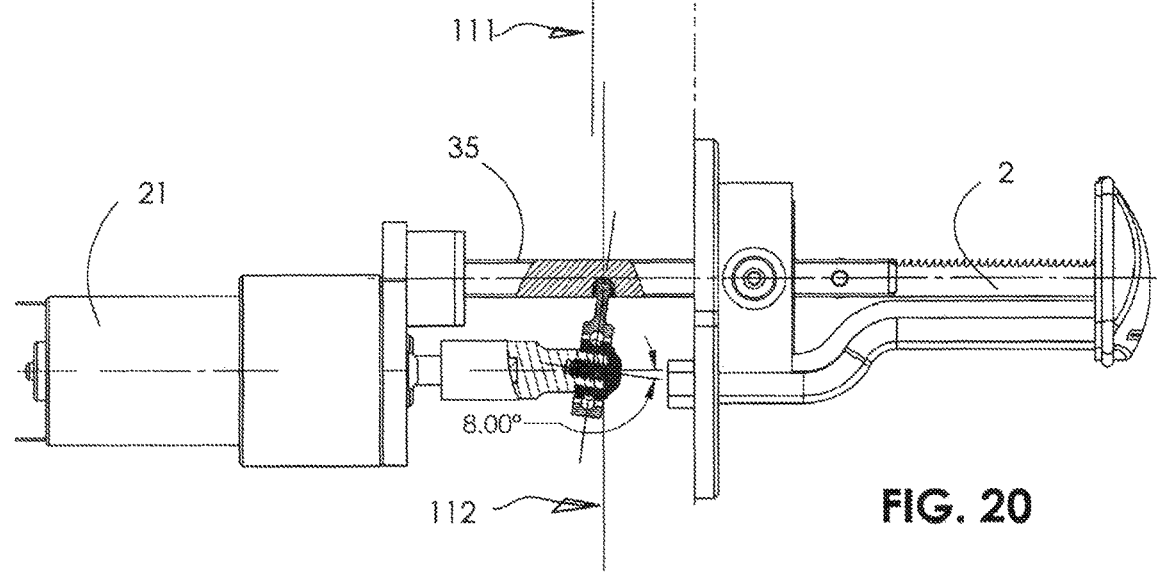
FIG. 20 illustrates a side view of reciprocating saw.

FIGS. 19 and 20 are additional side views of reciprocating saw of FIG. 18. FIG. 18 shows plunger at minus eight degrees 110, FIG. 19 shows plunger at zero degrees 111, and FIG. 20 shoes the plunger at plus eight degrees 112.

Figure 21:
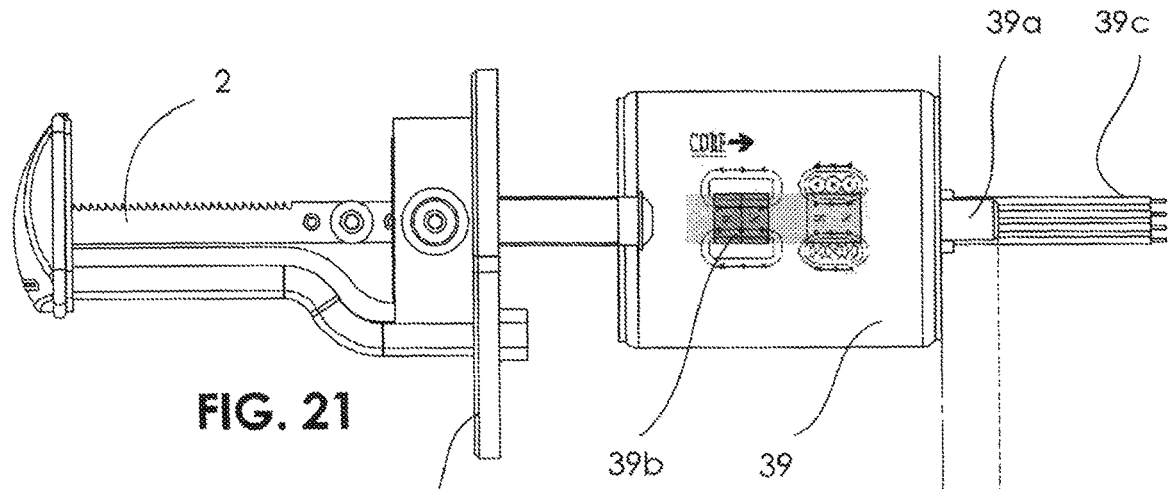
FIG. 21 illustrates a side view of reciprocating saw.
Figure 22:
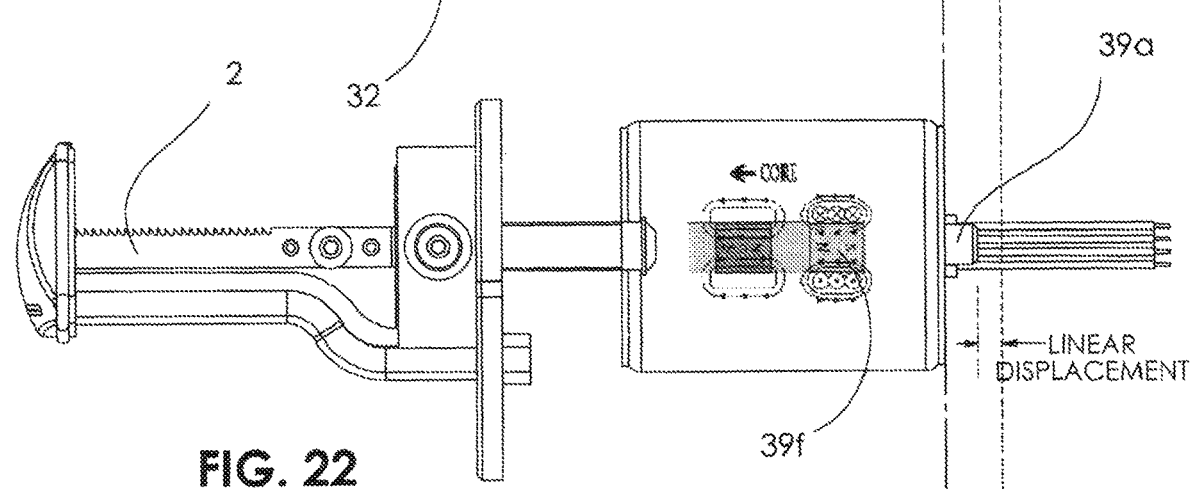
FIG. 22 illustrates a side view of reciprocating saw.
Figure 23:
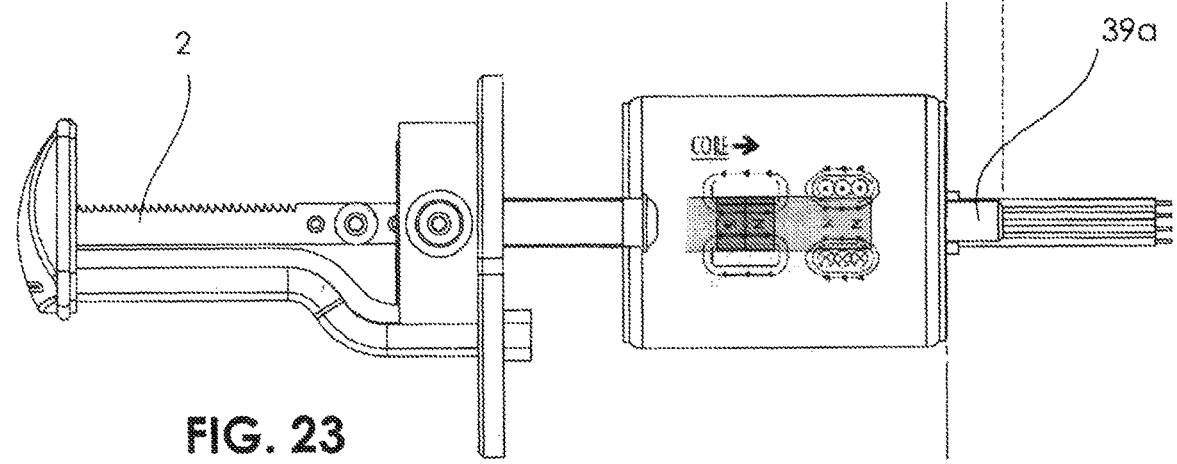
FIG. 23 illustrates a side view of reciprocating saw.

FIG. 21 illustrates a side view of a reciprocating saw, using electromagnetic vibrating solenoid. Solenoid permanent magnet core is attracted by the armature polarity. Illustrated in this view are blade 2, blade support mounting plate 32, housing 39, core shaft 39a, core moving permanent magnet (diagram showing polarity) 39b, and armature alternating polarity controller cable 39c, and fixed armature diagram showing reversed polarity 39f. FIGS. 21-23 show the polarity changing, resulting in a reciprocating up and down motion.

Other features and advantages of the invention should become apparent from the foregoing description of the preferred embodiments, taken in conjunction with the accompanying drawings, which illustrate, by way of example, the principles of the invention.

REFERENCE NUMBERS

1. Base
1a. Disposable base cover
1b. Saw support
1c. Base support mounting
1s. Blade tip clearance slot
1d. Clear camera window
2. Blade
3. Post/motor housing
4. Handle
5. Handle
6. Button/switch
7. Body
8. Trigger
9. Button/switch
10. Button/switch
12. Camera
12a. camera video & power cable
12b. camera video light & power cable 13. LED strip
13a. LED strip power
15. Cautery member
15a. Cautery member ceramic insulator
15b. Cautery member connector
16. Base connector
16b. Base connector protective shield
16c. Base connector receptacle
17. vibration generating motor
21. DC gear motor
31. Motor chassis
32. Blade support mounting plate
33. shaft
34. shaft ball bearing
34a. ball bearing inner race (fixed on item 33, Oscillating shaft)
34b. ball bearing outer race (attached to pivoting plunger with joint ball)
35. Linear shaft
35a. Linear shaft receptacle joint cup
36. shaft linear bearing
38. Disposable base cover mounting screw
39. Bi-directional latching solenoid
39a. Core shaft
39b. Core moving permanent magnet diagram showing polarity
39c. Armature alternating polarity controller cable
39f. fixed armature diagram showing reversed polarity
110. Shaft, item 35 initial position at 0 or 360 degree angle.
111. Shaft, item 35 displacement at 90 degree rotation from 0 or 360 degree position.
112. Shaft, item 35 displacement at 180 degree rotation from 90 or 270 degree position.

What is claimed is:

1. A device for cutting a sternum comprising: a) a body; b) a handle attached to the body; c) a blade positioned below the body to cut the sternum when a user holds the handle; d) a base below the blade configured to be positioned below the sternum; wherein the base can be placed under the sternum such that the blade can cut the sternum.

2. The device of claim 1, wherein the base has a leading edge in a direction towards a head of a person when cutting the sternum, the leading edge having an angle of about 20 degrees to about 60 degrees.

3. The device of claim 1, wherein the base has a leading edge that is triangular.

4. The device of claim 1, wherein the base further comprises a camera or a light source.

5. The device of claim 1, wherein the device further comprises a member configured to perform cautery, the member placed on the base in a position to contact blood vessels as the device cuts the sternum.

6. The device of claim 5, wherein the member comprises one or more strips of a material that heats up when electricity or radiofrequency passes through the material.

7. The device of claim 5, wherein the base comprises a portion located below the member, and wherein said portion extends out further than the member to insulate tissue that is below the base from the member.

8. The device of claim 1, wherein the base has a maximum width to maximum height ratio of 2 to 5.

9. The device of claim 1, wherein the blade is placed at a backwards angle (top of the blade further back) relative to a perpendicular in relation to a top of the base.

10. The device of claim 1, wherein the blade and/or the base is visible from a top of the device when the base is in a horizontal position.

11. The device of claim 1, wherein the body is non-linear and is configured to allow the user to view the base when cutting the sternum from a top of the device.

12. The device of claim 1, wherein the body has a void configured to allow the user to view the base.

13. The device of claim 1, wherein the device has two handles, with each of the handles placed on opposite sides of the body.

14. The device of claim 13, further comprising at least one switch on each handle, with one switch on the first handle configured to power the blade and one switch on the second handle configured to power a heating element of the base for performing cautery.

15. The device of claim 1, wherein the device comprises a post portion extending upward from the blade, the body further comprising a segment with a void where the blade is visible during operation through the void, wherein the segment with the void is attached to the post, and wherein the device comprises two handles, with one handle attached to the segment with the void and another handle to the post and/or the segment with the void.

16. The device of claim 1, wherein the device comprises a connector, and wherein the base is attached to the body with the connector, with the body and/or handle extending on two different sides of the blade.

17. The device of claim 1, wherein the device has two handles that are not directly attached to each other.

* * * * *